(12) United States Patent
Michalek et al.

(10) Patent No.: US 9,150,799 B2
(45) Date of Patent: Oct. 6, 2015

(54) WASTE PROCESSING APPARATUS AND METHOD FEATURING POWER GENERATION, WATER RECYCLING AND WATER USE IN STEAM GENERATION

(75) Inventors: Jan K. Michalek, Pataskala, OH (US); Theodore J. Thomas, Columbus, OH (US)

(73) Assignee: Estech USA, LLC, Canal Winchester, OH (US)

( * ) Notice: Subject to any disclaimer, the term of this patent is extended or adjusted under 35 U.S.C. 154(b) by 811 days.

(21) Appl. No.: 12/653,819

(22) Filed: Dec. 21, 2009

(65) Prior Publication Data

US 2010/0163396 A1 Jul. 1, 2010

Related U.S. Application Data

(60) Provisional application No. 61/203,547, filed on Dec. 23, 2008.

(51) Int. Cl.
*C10B 1/00* (2006.01)
*C10J 3/00* (2006.01)
*A61L 12/00* (2006.01)
*B09B 3/00* (2006.01)
(Continued)

(52) U.S. Cl.
CPC .. *C10J 3/00* (2013.01); *A61L 12/00* (2013.01); *B09B 3/00* (2013.01); *B09B 3/0091* (2013.01); *D21B 1/026* (2013.01); *F02C 3/28* (2013.01); *F02C 6/18* (2013.01); *C10B 49/00* (2013.01); *C10J 2300/092* (2013.01); *C10J 2300/0903* (2013.01); *C10J 2300/0946* (2013.01); *C10J 2300/0956* (2013.01); *C10J 2300/0973* (2013.01); *C10J 2300/0976* (2013.01); *C10J 2300/16* (2013.01); *C10J 2300/1671* (2013.01); *C10J 2300/1687* (2013.01); *C10J 2300/1892* (2013.01); *Y02E 20/12* (2013.01); *Y02E 20/14* (2013.01); *Y02E 50/11* (2013.01); *Y02E 50/12* (2013.01); *Y02E 50/14* (2013.01); *Y02W 30/20* (2015.05)

(58) Field of Classification Search
CPC .......... B09B 5/00; Y02E 30/00; Y02E 50/30; B01J 2/12; B01J 7/02; B01J 8/00; C10J 3/48; C10B 49/00
USPC ........... 48/197 R; 585/240; 422/11, 285, 286, 422/298
See application file for complete search history.

(56) References Cited

U.S. PATENT DOCUMENTS 228,542 A 6/1880 Lister
986,180 A 3/1911 Koenig
(Continued)

FOREIGN PATENT DOCUMENTS

WO   WO 00/72987   * 12/2000
WO   WO 03/024633   * 3/2003

*Primary Examiner* — Nina Bhat
(74) *Attorney, Agent, or Firm* — Standley Law Group LLP

(57) ABSTRACT

A system and method for processing solid waste products includes an autoclave, a combined heat and power generation system and a water treatment system. Water in the solid waste products is vaporized to raise steam, by heating the autoclave. Waste liquids, steam and cellulosic material are removed from the autoclave. The cellulosic material is combusted in the heat and power generation system, which generates steam and electricity, with the steam recycled to the autoclave. The steam and the waste liquids are processed in the water treatment system, with the cleaned water cycled to the heat and power generation system to be converted into steam.

5 Claims, 3 Drawing Sheets

(51) Int. Cl.
  *D21B 1/02* (2006.01)
  *F02C 3/28* (2006.01)
  *F02C 6/18* (2006.01)
  *C10B 49/00* (2006.01)

(56) References Cited

U.S. PATENT DOCUMENTS

| | | |
|---|---|---|
| 1,381,802 A | 6/1921 | Copelin |
| 1,536,894 A | 5/1925 | Lillie |
| 4,342,830 A | 8/1982 | Holloway |
| 4,540,495 A | 9/1985 | Holloway |
| 4,844,351 A | 7/1989 | Holloway |
| 4,852,344 A | 8/1989 | Warner |
| 4,898,107 A | 2/1990 | Dickinson |
| 4,974,781 A | 12/1990 | Placzek |
| 5,000,099 A | 3/1991 | Dickinson |
| 5,050,375 A | 9/1991 | Dickinson |
| 5,116,363 A | 5/1992 | Romweber et al. |
| 5,119,994 A | 6/1992 | Placzek |
| 5,190,226 A | 3/1993 | Holloway |
| 5,253,764 A | 10/1993 | Gement |
| 5,261,225 A | 11/1993 | Dickinson |
| 5,300,438 A | 4/1994 | Augspurger et al. |
| 5,361,994 A | 11/1994 | Holloway |
| 5,407,809 A | 4/1995 | Finn |
| 5,427,650 A | 6/1995 | Holloway |
| 5,445,659 A * | 8/1995 | Khan et al. .................. 48/197 R |
| 5,485,728 A | 1/1996 | Dickinson |
| 5,500,044 A | 3/1996 | Meade et al. |
| 5,540,391 A | 7/1996 | Anderson |
| 5,556,445 A | 9/1996 | Quinn et al. |
| 5,655,718 A * | 8/1997 | Anderson ........................ 241/17 |
| 5,669,969 A | 9/1997 | Meade et al. |
| 6,387,221 B1 * | 5/2002 | Schoenhard .................... 201/25 |
| 6,397,492 B1 | 6/2002 | Malley |
| 6,548,197 B1 | 4/2003 | Chandran et al. |
| 6,680,137 B2 | 1/2004 | Paisley |
| 6,730,223 B1 | 5/2004 | Anderson et al. |
| 6,923,004 B2 | 8/2005 | Chandran et al. |
| 6,960,234 B2 | 11/2005 | Hassett |
| 7,028,478 B2 | 4/2006 | Prentice, III |
| 7,189,270 B2 | 3/2007 | Bryan et al. |
| 7,208,530 B2 | 4/2007 | Norbeck et al. |
| 7,272,934 B2 | 9/2007 | Chandran et al. |
| 7,347,391 B2 | 3/2008 | Michalek et al. |
| 2004/0250700 A1 | 12/2004 | Renaud |
| 2005/0035032 A1 | 2/2005 | McGee |
| 2005/0059849 A1 | 3/2005 | Liu |
| 2009/0217848 A1* | 9/2009 | Clark et al. .................... 110/346 |

* cited by examiner

WASTE PROCESSING APPARATUS AND METHOD FEATURING POWER GENERATION, WATER RECYCLING AND WATER USE IN STEAM GENERATION

RELATED APPLICATION DATA

This application claims the priority benefit of U.S. Provisional Application Ser. No. 61/203,547, filed Dec. 23, 2008, which is hereby incorporated in its entirety herein by reference.

TECHNICAL FIELD

The present invention relates to the treatment of municipal solid waste and the like, and to the raising of steam for electric power generation.

BACKGROUND OF THE INVENTION

The present invention relates to systems and methods for treating process material and, more particularly, to systems and methods for treating municipal solid waste material, medical waste material, reclaimed paper and the like.

As a result of increasing scarcity of landfills and more stringent environmental regulations, efforts have been made to reduce the volume of process material, such as municipal solid waste ("MSW") and paper material, such as newsprint and other reclaimed and recycled paper products as a step in the process of disposing of the material, either by depositing it in landfills, incinerating it or recycling it.

Systems and methods have been developed to break down such material for disposal, or in the case of paper products, use as insulation.

One of the disadvantages of systems of the prior art is that they fail to make maximum most efficient use of the energy used in these systems. Prior art systems generally release copious quantities of steam during the cool-down cycle, and the release of steam is a significant energy cost. Accordingly, there remains a need for waste treatment systems that make more efficient use of energy in their operation.

Another disadvantage of systems of the prior art is that they have been less than completely satisfactory in their efficient and complete use and treatment of water that is contained in the waste mass or that is otherwise supplied to the waste treatment autoclave. In addition, efficient use of water is also required where operation of waste treatment systems is desired in areas where suitable water supplies are scarce or unavailable, or otherwise where waste water cannot be legally or economically released. There remains a need for waste treatment systems that may more efficiently use and recycle water, especially the "contact" water from condensate that was in contact with waste and which can even be operated in areas of water scarcity and/or where water should not be released.

Another disadvantage of systems of the prior art is that the fibrous "product" of the waste autoclave process is a clean cellulose, for which to date there is little commercial market. Some systems exist that will oxidize the cellulose thus releasing energy; there remains a need for an efficient system to convert this energy into saleable commodities.

Another disadvantage of systems of the prior art is that the autoclave process releases small quantities of volatile organics. An effective and efficient system to separate volatiles (and air) from contact steam is needed.

The present invention accordingly represents an improvement over prior art apparatus and methods, such as those described in U.S. Pat. Nos. 5,540,391; 5,116,363; 5,253,764; 5,190,226; 5,361,994; 5,427,650; 5,407,809; and 6,397,492, and in published European Patent Application No. 02758620.5; all of which are incorporated herein by reference. The present invention also represents an improvement relating to and which may be used in conjunction with the inventions described in co-pending application Ser. Nos. 11/122,341, 11/716,101, 11/981,144, 61/123,351, 61/195,791, 12/313,911 and PCT/US06/16773 that are hereby incorporated in their entirety by reference.

The present invention also relates to and may be used in conjunction with co-pending application Ser. No. 12/315,258, which is hereby incorporated in its entirety by reference and which focuses on the steam/water recycling aspects of a total waste-to-energy system.

SUMMARY OF THE INVENTION

The apparatus and methods of the present invention are summarized generally below. Each of the elements, features and characteristics of the invention may be combined independently with one another and includes several general inventions.

The present invention includes the combination of autoclaves with an energy conversion system, preferably that of a combined heat and power system (CHP), to combust the clean cellulosic fibrous product of a solid waste autoclave and to use some of the energy to generate electricity for export and sale, and steam to operate the autoclave and for other ancillary purposes of an entire combined system. Other systems exist that convert chemical energy of clean cellulose to liquid or gaseous fuels; these processes also allow electricity and steam to be raised to support the needs of the autoclave system.

The present invention also includes the combination of autoclaves with a partial energy conversion system, preferably that of a combined heat and power system (CHP), to combust the clean cellulosic fibrous product of a solid waste autoclave and to use some of the energy to generate electricity for export and sale, and steam to operate the autoclave and for other ancillary purposes of an entire combined system. Excess cellulose is converted by standard processes to liquid or gaseous fuels.

One purpose that may be served using the system and method of the present invention may be to utilize excess steam to produce additional electrical energy.

Still another purpose to which the recovered steam condensate may be used is to pre-heat combustion air for the CHP system.

The present invention preferably includes a combination of a combined heat and power (CHP) system that preferably gasifies and then combusts the fibrous product of an autoclave for processing waste. The CHP uses a "topping cycle", such as a gas engine or gas turbine, in order to generate electricity, and a "bottoming cycle", such as may be provided by a Heat Recovery Steam Generator (HRSG), to heat water to create steam, and/or to heat steam to create superheated steam Additional equipment may include a vapor recompressor (VR), in order to recompress spent steam such as may be generated from the vessels. Additional equipment may include chemical processes to convert cellulose to liquid or gaseous fuels.

Excess steam, not needed by the vessels, optionally may be reintroduced into the turbine to produce additional electricity.

The present invention includes what may be described as a four part system wherein (1) an autoclave system for treating municipal waste to create combustible material to be combusted, such as by gasification or otherwise, to generate power in a combined (2) electric power generation and steam production/recycling system, which produces energy to be used with (3) a water/steam treatment system that may be used to treat condensate from issuing from the autoclave, together with an optional chemical conversion process to convert cellulose to liquid or gaseous fuels.

An example of a device used in the power generation system includes a gas turbine (Brayton Cycle Engine) adapted to accept gas from a pressurized clean cellulose gasifier, and providing compressed air to the gasifier, adapted to a generator for the production of energy, with steam extraction from the heat recovery steam generator for use in the vessels and/or to produce additional electrical energy from the turbine.

The system effectively combines an autoclave system for treating municipal waste with a combined heat and power (CHP) system. The power generation component may be any one or more means for obtaining energy from the fiber produced from the autoclave, such as devices adapted to carry out such processes, such as anaerobic digestion combustion, gasification partial combustion, pyrolysis c and the like. Accordingly, the CHP system may include any one or combination of devices to release energy from the processed waste material which is principally clean cellulosic fiber, and the energy released can be used to generate steam and/or power.

Preferably, electrical energy may be generated using a Brayton cycle turbine to drive a generator, although other devices, such as a Sterling and Otto cycle device, may be applied for the same purpose, alone or in combinations. Waste heat from any prime mover (for example, a Brayton cycle turbine) can be used to generate steam in an HRSG.

In contrast to earlier systems that typically used fossil fuel combustion to generate electricity for these systems, the system of the present invention uses the CHP system to produce both the electricity and steam required to provide mechanical needs for the vessel system, such as the operation of the autoclave and the water treatment system, waste to energy conversion, etc.

The system of the present invention is capable of supplying steam and other energy needs of the autoclave system, such as that typically required for autoclave pre-heat and operation, and boiler pre-heat.

In addition, rather than exhausting the condensate waste water to the sanitary sewer, the system may be adapted to treat and recycle the waste water/waste steam for re-conversion into higher energy steam for reuse in the system. The system may optionally comprise a vapor recompressor to raise steam condensate to vessel operating pressure. The compressed condensate may then be condensed to water, chemically treated, and reheated to steam. The condensation and reheat of the compressed condensate may be provided by the technology known as a "heat pump". In the preferred cycle, the heat pump operates at a constant pressure and serves simply to transfer heat. The system thus may use a water treatment component to recycle the water and steam for reuse in the autoclave/HRSG/turbine system, rather than have the waste water discharged to the sanitary sewer facility, and the waste steam discharged to air, as is typically done.

A system may also optionally include a heating unit adapted to be provided with energy generated by the power generation system to heat the autoclave.

The system thus is capable of extracting clean cellulose from the waste stream, converting the cellulose to electrical energy and steam, and using some of that energy to operate the autoclave and water treatment systems.

The system may be produced using portable and/or modular components so that it may be assembled at a pre-determined site, to provide a customized system adapted to the particular resource availability and allowable emission profile. For instance, the system may be adapted for use where water is unavailable or scarce, or where the emission standards are exceptionally restrictive.

The recycled water may be returned to the steam generation system which obtains energy from the power generation system. The power generation system may also return excess energy to the local power grid. The energy from the system may be diverted or reused within the system.

The system of the present invention can be constructed and its operation controlled so as to be capable of operating in a zero discharge fashion.

The system of the present invention may be automatically monitored with respect to such parameters as chlorine content, metals content and water analysis, as well as the quality of air emissions from either the autoclave system or the combustion/power generation system.

The system may also be adapted to provide a sufficiently clean cellulosic material for combustion by cleansing the fibrous product resulting from autoclave treatment.

Another aspect of the invention is that clean cellulosic fiber is produced that is suitable for combustion, or for chemical or biological conversion into fuels.

Method of Treating Waste while Removing Water for Steam Generation

The present invention includes a method of processing solid waste products in an autoclave, comprising the steps: (a) loading the autoclave with a charge of solid waste products containing water; (b) sealing the autoclave; (c) rotating the autoclave while heating the autoclave such that the charge of solid waste products containing water creates steam in the autoclave, and whereby so waste liquid water or steam and cellulosic material are produced; (d) conducting condensate from the autoclave ("non-contact" from an external shell heater and/or "contact" from the evaporation of water in the autoclave) to water cleaning systems and then to a heat recovery steam generator and/or vapor recompressor so as to generate steam therefrom; and (d) reintroducing the steam generated by the heat recovery steam generator into an autoclave. It is preferred that the steps are performed in a closed loop zero discharge system. The system may be rendered closed by using conduit arrangements to completely close the water circulation to the system described herein. The system takes advantage of the water typically contained in the waste stream, such as in municipal waste.

In another variation of the method of the present invention, the present invention includes a method of processing solid waste products in an autoclave comprising the steps: (a) treating solid waste products in an autoclave so as to produce treated solid waste products comprising cellulosic material, and waste water and used steam; (b) converting the treated and cleansed solid waste products to a converted cellulosic material selected from the group consisting of (1) cellulosic ethanol (2) cellulosic chemicals and (3) cellulosic diesel, (c) converting the converted cellulosic material to energy; (d) conducting waste water from the autoclave to a water cleaning system and then to a heat recovery steam generator so as to generate steam therefrom; and (e) reintroducing the steam generated by the heat recovery steam generator into the autoclave.

The method of the present invention may also include a method of processing solid waste products in an autoclave comprising the steps: (a) treating solid waste products in an autoclave so as to produce treated solid waste products comprising cellulosic material, and waste water and used steam; (b) converting the treated and cleansed solid waste products to energy; (c) conducting waste water from the autoclave to a water cleaning system and then to a steam production system, which produces electrical energy from the combustible material, and produces steam from waste heat, the steam production system selected from the group consisting of steam production systems adapted to produce steam by combustion of (1) cellulosic ethanol (2) cellulosic chemicals and (3) cellulosic diesel so as to generate steam therefrom; and (d) reintroducing the steam generated by the heat recovery steam generator into the autoclave.

System Combining Waste Treatment Autoclave and Power Generation System

The present invention also includes a system for processing solid waste products, the system comprising: (a) a rotatably mounted cylindrical autoclave adapted to contain and heat a charge of solid waste products containing water condensate and cellulosic material are produced thereby (non-contact condensate, from an external shell heater and/or contact condensate from the evaporation of water in the autoclave); (b) a water cleaning system or systems adapted to clean the waste liquid water or steam; (c) a heat recovery steam generator adapted to accept waste liquid water or steam from the water cleaning system(s), and to generate steam therefrom; e) a vapor recompressor to raise the pressure of spent (non-contact) steam and (d) a conduit adapted to reintroduce the steam generated by the heat recovery steam generator and/or vapor recompressor into an autoclave.

The system preferably is a closed loop zero discharge system.

Preferably, the system additionally comprises a Brayton Cycle turbine with generator adapted to clean cellulose and/or its gasification products to provide energy therefrom, and may advantageously include a heating unit adapted to be provided with energy generated by the HRSG to heat the autoclave.

It is also preferred that the method additionally comprises gasifying and then combusting the cellulosic material so as to provide energy for the production of electricity and to the heat recovery steam generator, and that one conducts the waste liquid water or steam condensate through separations, treatment, and recompression.

It is also preferred that the gasification and combustion occurs under pressurized conditions, with the pressurization provided by the Brayton Cycle Compressor.

To clean the water/steam from the autoclave contents, the system may include a heat exchange, to both preheat combustion air and to condense "contact" steam from the vessel. Experimentation has found that the condensation produces the unexpected result of providing for the separations of air and such volatile organics as may be released in the vessel from the condensed water. The condensed water may then be polished with conventional boiler water technologies for re-use. The low-pressure gaseous stream from the preheater heat exchange contains air, steam, and small quantities of volatile organics. This stream may optionally be directed to the power system, preferably the Brayton Cycle Engine Compressor, to allow the volatile organics to be oxidized in the gasification/combustion process.

The combined process produces excess steam from the copious quantities of water found in the supply of MSW. This excess steam may be pressurized and directed to the turbine in order to limit turbine temperatures. It may also be injected into the gasifier and/or combustor as saturated or superheated steam in order to assist with the gasification chemistry and/or to provide additional mass flow while limiting peak operating temperatures.

The steam provided to the autoclave from the HRSG may be saturated steam, dry steam or super-heated steam, and may be provided statically or as a stream through the autoclave, or even in the form of discrete steam pulses into the autoclave system such as pulses of super-heated steam.

The present invention also includes alternatives to produce liquid or gaseous fuels. Prime examples include conversion systems selected from the group consisting of (1) cellulosic ethanol production systems (2) cellulosic chemical production systems and (3) cellulosic diesel production systems, adapted to convert the combustible material respectively into cellulosic ethanol, cellulosic chemicals and cellulosic diesel. Each of these is known to have waste heat, for conversion into steam, and/or waste products for combustion and conversion into steam and electricity.

The present invention thus includes a system for processing solid waste products in an autoclave and recycling the condensate water and steam and using energy processed therefrom, comprising: (1) an autoclave system for treating municipal waste with steam to create a cellulosic material, which autoclave generates waste water; (2) a conversion system selected from the group consisting of (a) cellulosic ethanol production systems (b) cellulosic chemical production systems and (c) cellulosic diesel production systems, adapted to convert the combustible material into a cellulosic material selected from the group consisting of respectively cellulosic ethanol, cellulosic chemicals and cellulosic diesel, and (3) a power generation and steam production system (which may include a CHP power generation system), which produces electrical energy from the cellulosic material and/or the waste products of cellulose conversion, and produces steam from waste heat, the steam production system selected from the group consisting of steam production systems adapted to produce steam by combustion of at least one cellulosic material selected from the group consisting of (a) cellulosic ethanol (b) cellulosic chemicals and (c) cellulosic diesel; and (4) a water treatment system that treats the condensate water and returns it for use in the steam production system, treats condensate steam and repressurizes it for use in the steam system.

System Combining Waste Treatment Autoclave and Cellulosic Steam Generator/Converter The present invention also includes a system for processing solid waste products, the system comprising: (a) a rotatably mounted cylindrical autoclave adapted to contain and heat a charge of solid waste products containing water so condensate liquid water or steam and cellulosic material are produced; (b) a conversion system selected from the group consisting of (1) cellulosic ethanol production systems (2) cellulosic chemical production systems and (3) cellulosic diesel production systems, adapted to convert the cellulosic material respectively into cellulosic ethanol, cellulosic chemicals and cellulosic diesel; (c) a water cleaning system adapted to clean the waste liquid water or steam; (d) a steam production system selected from the group consisting of steam production systems adapted to produce steam by combustion of (1) cellulosic ethanol (2) cellulosic chemicals and (3) cellulosic diesel and/or the waste products of cellulose conversion so as to generate steam therefrom, and a heat recovery steam generator, adapted to accept waste liquid water or steam from the water cleaning system, and to generate steam therefrom; and a conduit adapted to reintroduce the steam generated by the heat recovery steam generator into the autoclave.

The present invention also includes a system for processing solid waste products, the system comprising: (a) a rotatably mounted cylindrical autoclave adapted to contain and heat a charge of solid waste products containing water so condensate liquid water or steam and cellulosic material are produced; (b) a water cleaning system adapted to clean the waste liquid water or steam; (c) a heat recovery steam generator adapted to accept waste liquid water or steam from the water cleaning system, and to generate steam therefrom; (d) a conduit adapted to reintroduce the steam generated by the heat recovery steam generator into the autoclave; (e) a heating unit adapted to be provided with energy generated by the heat recovery steam generator to heat the autoclave; and (f) an evaporator to separate the waste liquid water or steam from the cellulosic material prior to combusting the cellulosic material.

The present invention also includes a system for processing solid waste products, the system comprising: (a) a rotatably mounted cylindrical autoclave adapted to contain and heat a charge of solid waste products containing water so condensate liquid water or steam and cellulosic material are produced; (b) a conversion system selected from the group consisting of (1) cellulosic ethanol production systems, (2) cellulosic chemical production systems and (3) cellulosic diesel production systems, adapted to convert the cellulosic material respectively into cellulosic ethanol, cellulosic chemicals and cellulosic diesel; (c) a water cleaning system adapted to clean the waste liquid water or steam; (d) a steam production system selected from the group consisting of steam production systems adapted to produce steam by combustion of (1) cellulosic ethanol (2) cellulosic chemicals and (3) cellulosic diesel so as to generate steam therefrom, (d) a heat recovery steam generator, adapted to accept waste liquid water or steam from the water cleaning system, and to generate steam therefrom; and (e) a conduit adapted to reintroduce the steam generated by the heat recovery steam generator into the autoclave.

The system preferably is a closed loop zero discharge system.

The system also preferably additionally comprises a steam turbine adapted to accept steam from said heat recovery steam generator and to provide energy therefrom.

The present invention includes methods of using an MVR to reclaim spent, non-contact steam in a waste autoclave system.

The present invention also includes methods of using a heat exchanger to condense contact steam from a waste autoclave system, and using the heat exchanger to warm combustion air, thereby retaining thermal efficiency.

The present invention further includes methods of using a heat exchanger to condense contact steam from a waste autoclave system, and using the heat exchanger to condense the contact condensate, thereby allowing the separations of volatile organics and air from the contact condensate so that the condensate can be reprocessed and reused.

The present invention includes an autoclave system that preferably operates at contents temperatures in the range of 300-335 F, thereby maximizing the efficiencies of the overall vessel thermal process within the operating limits posed by the vessel content plastics. The autoclave system of the present invention also preferably provides non-contact heating steam in the range of 335-450 F, that may be controlled automatically by monitoring contents temperatures, thereby maximizing the flow of heat from the heating steam to the contents while operating within the operating limits posed by the vessel content plastics. The autoclave system of the present invention preferably recovers superheated steam in the range of 212-1200 F from waste heat, thereby providing a means and method of increasing gasification rates, and increasing energy recovery via a Brayton Cycle engine while limiting its turbine inlet temperatures.

According to the invention, steam inlets are connected to one or more saturated or superheated steam supplies and to one or more steam receivers. In this way, the autoclave is pressurized and depressurized from one or more openings. Each opening may be provided with bidirectional steam flow conduits and valves.

The present invention is a waste treatment autoclave and associated system that combines a waste treatment autoclave such as disclosed herein or otherwise known and used in the art, with a power island to produce a zero-net-water electrical plant. The generation of electricity from steam requires both a supply water and a "blowdown" discharge water. More recently, gas turbines have been used to create electric power without water. However, more efficient use of gas turbines typically requires for example a steam "bottoming cycle", again requiring water.

The system and process of the present invention may be operated to be a net "producer" of water, in that the water content of incoming waste is removed and can be recovered for beneficial use. Accordingly, the waste treatment autoclave does need additional steam and water beyond that which may be obtained through original water content and recycling. The merged system of the present invention extracts both steam and water. As an unintended consequence, the water balance of the combined system can be adjusted such that the system does not require additional water, and that excess water is eliminated as steam. This feature allows for an avoidance of a waste treatment system for installations where water/waste water utilities are otherwise unavailable.

Figure 1:
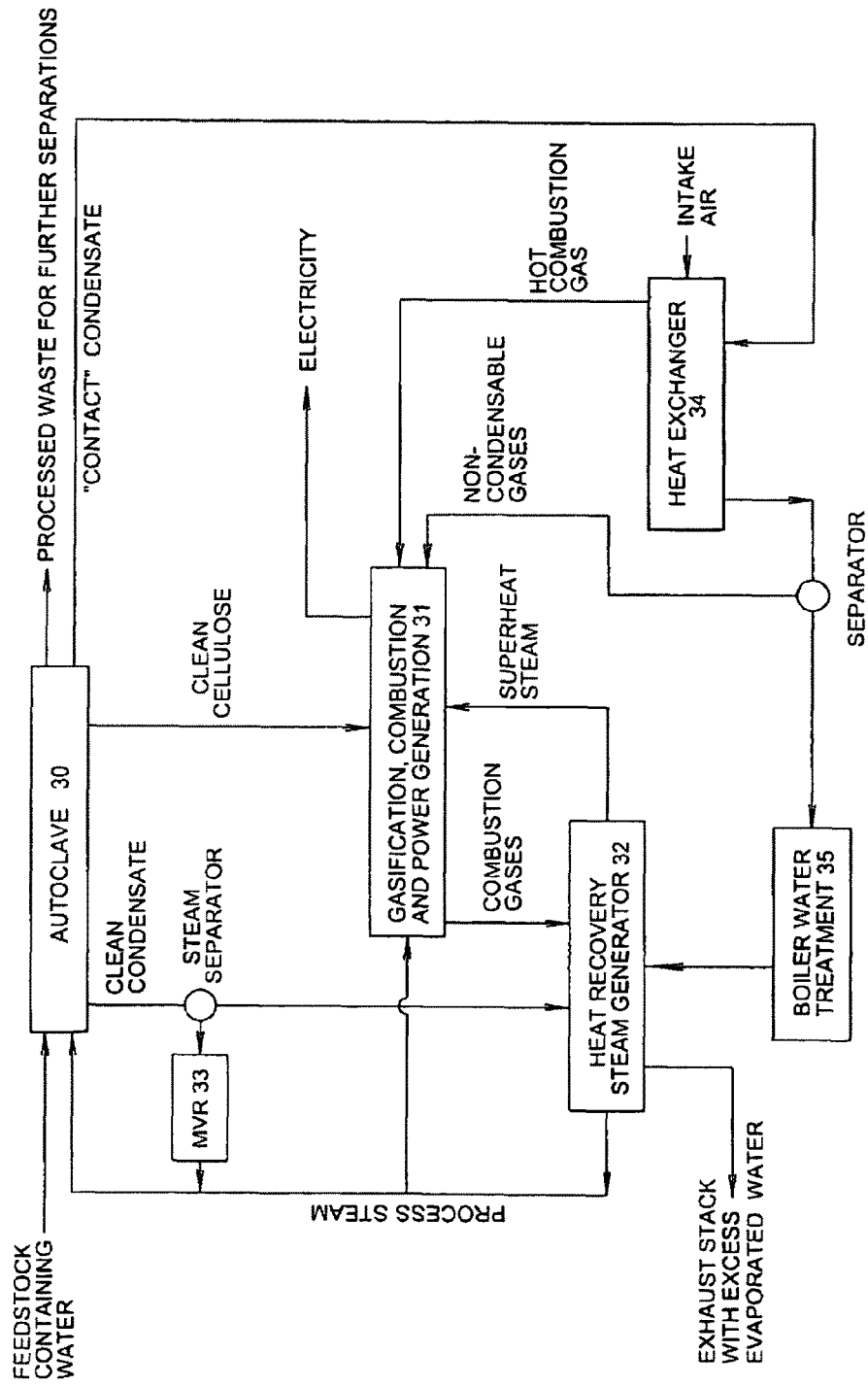
FIG. 1 is a functional schematic of a waste processing system with which the present invention may be used, for processing solid waste products in accordance with another embodiment of the present invention.
Figure 2:
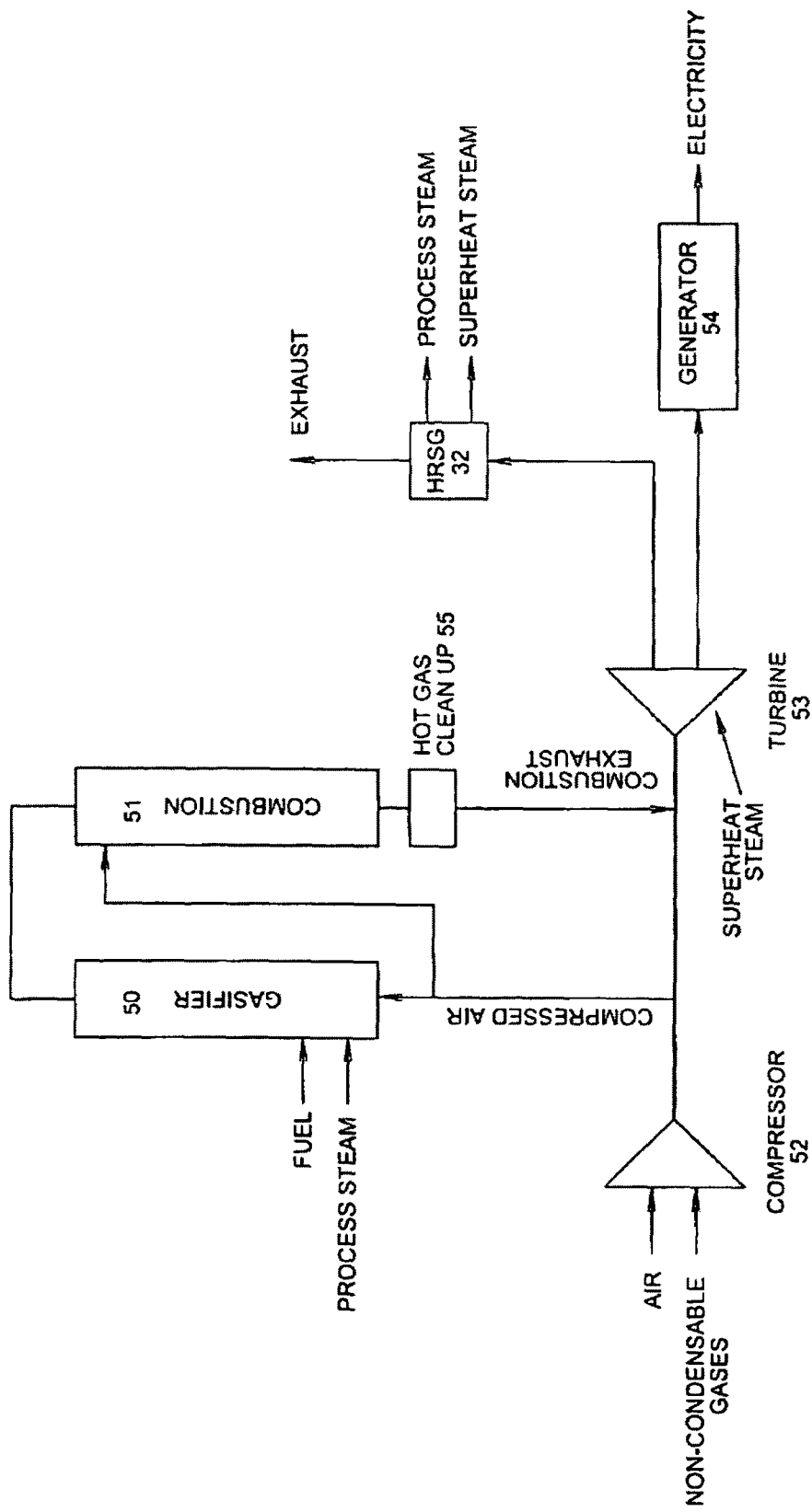
FIG. 2 provides detail of the power island 31 of FIG. 1. A given charge of waste products may contain a wide variety of constituents, such as wood, paper, organic matter, water, etc. Each charge of waste products presents its own heat capacity and transfer profile, while there is required an overall heat absorption of the mass in order to provide an effective treatment of the waste products charge.
Figure 3:
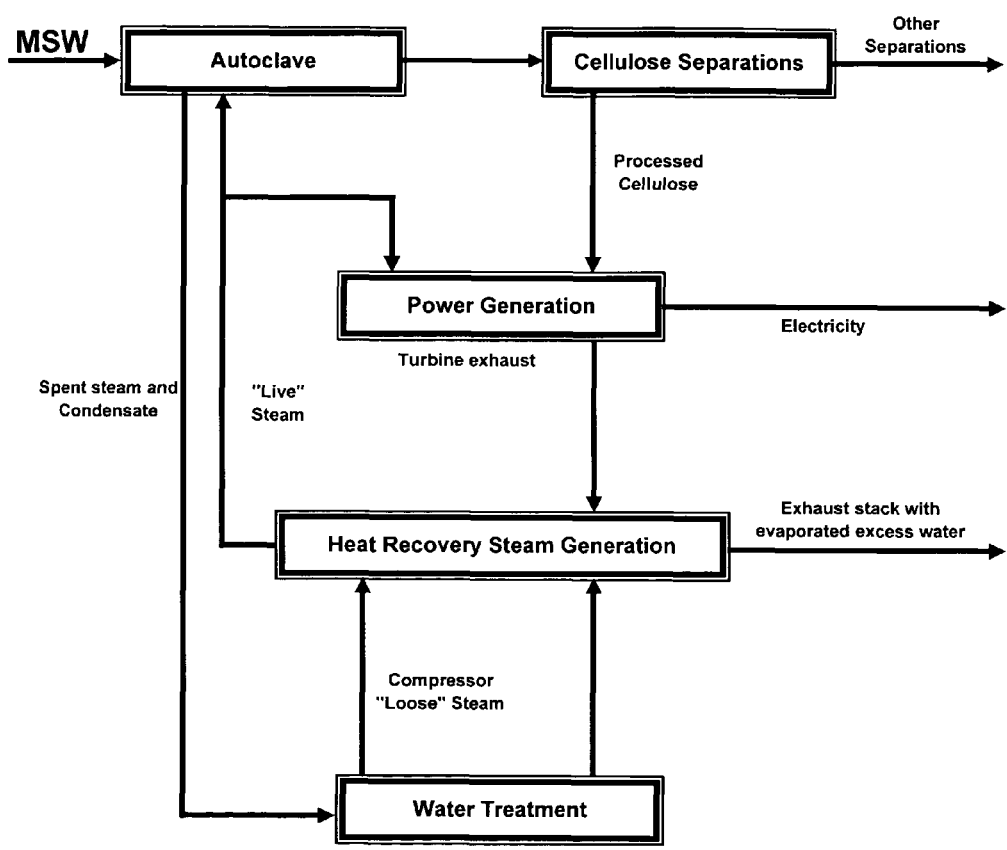
FIG. 3 is a general schematic of a system in accordance with the present invention. Though not shown on FIG. 3, but as part of the invention, cellulose may be diverted to a conversion to liquid or gaseous fuels, and steam for the conversion may also be diverted.

Referring to FIGS. 1 and 2, these figures show schematics of a system that include a waste treatment autoclave and conduits adapted to direct steam generated thereby to a Brayton cycle turbine or similar power generation device.

The power generated by the Brayton cycle turbine may then be used to supply steam power to heat the waste treatment autoclave and/or electric power to provide mechanical action, such as in the rotation or leveling of the waste treatment autoclave, as well as to provide steam and electricity for commercial sale.

FIG. 1 shows autoclave 30 that receives a feedstock of waste material containing water. The autoclave 30 releases processed waste as well as processed cellulose. The processed cellulose may be converted to a gaseous fuel by conventional means such as pyrolysis, gasification, and/or anerobic digestion, and the gas so produced may be combusted to produce mechanical power, with the mechanical power used to drive an electric generator to produce electric power.

The processed cellulose may be converted to energy or fuel by other methods as well. All of these processes begin with biomass, and many of them have considered garbage (MSW) as a feed source, and the system of the present invention may be applied to provide a beneficial pretreatment for these systems.

These systems may include: (1) cellulosic ethanol systems including (a) biologic and (b) thermochemical variations thereof, (2) cellulosic chemicals and (3) cellulosic diesel.

Typically, in biologic cellulosic ethanol systems, there are pretreatments which aid in the separations of lignin from cellulose fibers. The lignin may be burned to produce steam for other parts of the process. The systems and methods of the present invention may incorporate steam production by combusting fiber or such fiber components that are not used for ethanol production for the purpose of raising steam for the vessels, whether steam alone or by CHP.

As to the thermochemical variations, this type of system includes a gasification step (similar to that used in one embodiment of the present invention) and then causes the chemical fragments at high temperature and pressure to reform into gaseous fuels that will condense on cooling. The systems and methods of the present invention may incorporate steam production by combustion of gasified biomass, or the reformed fuels and byproducts of gasification, for the purpose of raising steam for the vessel(s), whether by steam alone or by CHP.

As to the cellulosic chemicals the foregoing is also directly applicable to the production of cellulosic chemicals, generally speaking.

Extant pathways for conversion of cellulose to oil proceed through pyrolysis. The systems and methods of the present invention may incorporate steam production by combustion of pyrolysis gases, or the byproducts of pyrolysis, for the purpose of raising steam for the vessel(s), whether by steam alone or by CHP.

Waste heat from the combustion gases of the power generation cycle is captured in a heat recovery steam generator 32. Steam from the HRSG is used in the autoclave 30 while excess steam is exhausted through the power system to produce additional electricity.

In the preferred configuration, the combustion system of FIG. 2 includes a pressurized gasifier 50 which is fed solid fuel, compressed air (typically maintained between 5 and 15 bar), and is pressurized by a turbocompressor 52 such as may be found on a Brayton cycle engine, and by steam at combustion system pressure. The gasifier converts virtually all of the solid fuel to partially oxidized gaseous fuel and suspended particulates, including carbon.

In the preferred system, the gasifier product enters a high air/fuel ratio combustor 51, with the excess air provided by the turbocompressor 52 as noted above. The turbulence, high oxygen concentration, and time in the combustor provide for the complete combustion of the gaseous fuel and combustible components of the suspended particulate.

In the preferred system, non-combustibles are removed in a hot-gas particle control device, which may be a lined cyclone or a steel or ceramic candle filter. As the temperatures in this section are in the range of 1400-1600° F., and preferentially 1550° F., specialty steels may be used.

In the preferred system, the cleaned hot pressurized gas from the hot gas cleanup 55 are directed to the Brayton cycle turbine 53.

In the preferred system, excess water as steam is provided to the turbine system 33 as high pressure steam or superheated steam, and is preferentially medium pressure superheated steam. The provision of steam to the power system provides the benefit of lowering combustion temperature even while larger quantities of fuel are used, while providing additional electricity.

In the preferred system, steam added to the gasifier 50 assists in gasification of carbonaceous solids.

Non-contact steam circulating through the autoclave is easily recycled. Condensate passes through a steam trap, providing condensed water for the HRSG. Some 0-50% of the condensate, preferably 15%, is present as steam, at a pressure slightly lower than the vessel operating pressure. A small mechanical vapor recompressor 33 may be used to recompress the steam to vessel operating pressure.

As disclosed in related patents, the vessel operating pressure is ideally as high as possible, but is limited by the decomposition temperature of plastics. The vessel operating pressure is set to be as high as possible without decomposing plastics, preferentially in the range of 300-335 F.

The steam temperature in the non-contact shell heater of the vessel may be higher than the allowable contents temperature. Thus, the preferred design provides that the HRSG and/or MVR may generate higher temperature non-contact steam, in the range of 330-450 F, while closely monitoring the temperature of contents to limit the temperature of non-contact steam based on contents temperature.

Contact condensate (which is nearly 100% vapor) has been found to contain volatile organics and air, both of which are deleterious to boiler systems. In the preferred system, the contact condensate is cooled and condensed with combustion air in a heat exchanger 34. Noncondensibles are drawn off and preferably are combusted for heat recovery. Contact condensate is treated with standard boiler chemicals to neutralize pH and to chemically combine residual free oxygen in boiler water treatment 35. The clean, condensed contact water is then re-used.

System "blowdown" is provided at the HRSG 32, wherein copious quantities of steam with dissolved solids, and smaller quantities of water with suspended solids, are released for power recovery to the power system.

The steam/water separator following the heat exchanger 34 provides a gaseous stream with air, steam, and small quantities of volatile organics. This stream is of small volume, as compared to the combustion air, and may be mixed with combustion air so as to assure combustion of the contained volatile organics.

The system may also include the necessary energy conduits, such as electric cables and steam conduits, for transport and distribution of energy throughout the system as required for operation of the autoclave.

While the process description was offered in the context of the preferred embodiment using a Brayton Cycle turbine, one may adapt the process easily to other power generation systems. For example, power block 31/HRSG block 32 could be replaced with a conventionally fired boiler using any fuel, including the cellulose product.

It is apparent that while specific embodiments of the invention are disclosed; various modifications of the apparatus or parameters of the process may be made which will be within the spirit and scope of the invention. Therefore the spirit and scope of the present invention should be determined by reference to the claims below.

What is claimed is:

1. An integrated system for processing water-containing solid waste products, comprising:
  an autoclave system, in which the solid waste products are treated with steam, generating combustible material and waste water;

a combined heat and power ("CHP") generation system, comprising:
- a gasifier, in which the combustible material is converted into gaseous fuel energy;
- a Brayton cycle turbine to generate electricity from the gaseous fuel energy, at least a part of the electricity being used to turn the autoclave ; and
- a heat recovery steam generator that generates steam waste heat and supplies steam to the autoclave and the gasifier; and
- a water treatment system, which receives waste water from the autoclave system, the water treated therein being returned to the heat recovery steam generator and in which steam condensate is treated and returned to the heat recovery steam generator.

2. A system as claimed in claim 1 which includes performing said steps in a closed loop zero discharge system.

3. A system as claimed in claim 1, further comprising a conduit that introduces steam generated by said heat recovery steam generator into said autoclave.

4. A system as claimed in claim 1, further comprising an electrical conduit to conduct electricity generated by said power generation and steam production system to a local electric grid or electric storage device.

5. A system as claimed in claim 1, further comprising a conversion system for converting the combustible material into cellulosic ethanol, cellulosic chemicals and cellulosic diesel, the conversion system selected from the group consisting of: a cellulosic ethanol production system, a cellulosic chemical production system and a cellulosic diesel production system.

* * * * *